United States Patent
Sakamoto et al.

(10) Patent No.: US 9,745,407 B2
(45) Date of Patent: Aug. 29, 2017

(54) URETHANE-TYPE POLYMERS AND USE THEREOF

(71) Applicant: ADEKA CORPORATION, Tokyo (JP)

(72) Inventors: Takao Sakamoto, Tokyo (JP); Yasuhiro Tsushima, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/440,432

(22) PCT Filed: Nov. 25, 2013

(86) PCT No.: PCT/JP2013/081670
§ 371 (c)(1),
(2) Date: May 4, 2015

(87) PCT Pub. No.: WO2014/084174
PCT Pub. Date: Jun. 5, 2014

(65) Prior Publication Data
US 2015/0299375 A1    Oct. 22, 2015

(30) Foreign Application Priority Data

Nov. 29, 2012 (JP) ................................ 2012-261244
Apr. 23, 2013 (JP) ................................ 2013-090006

(51) Int. Cl.
| | |
|---|---|
| C08G 18/32 | (2006.01) |
| C08G 18/73 | (2006.01) |
| A61K 8/87 | (2006.01) |
| C08G 18/66 | (2006.01) |
| C08G 18/08 | (2006.01) |
| C08G 18/28 | (2006.01) |
| A61Q 19/00 | (2006.01) |
| A61K 8/06 | (2006.01) |
| C08G 18/48 | (2006.01) |
| C08G 18/76 | (2006.01) |

(52) U.S. Cl.
CPC ............. *C08G 18/73* (2013.01); *A61K 8/062* (2013.01); *A61K 8/87* (2013.01); *A61Q 19/00* (2013.01); *C08G 18/0866* (2013.01); *C08G 18/283* (2013.01); *C08G 18/2835* (2013.01); *C08G 18/3206* (2013.01); *C08G 18/4833* (2013.01); *C08G 18/6674* (2013.01); *C08G 18/7614* (2013.01); *A61K 2800/10* (2013.01); *A61K 2800/48* (2013.01)

(58) Field of Classification Search
CPC .............. C08G 18/283; C08G 18/2835; C08G 18/3206; C08G 18/4833; C08G 18/6674
See application file for complete search history.

(56) References Cited

FOREIGN PATENT DOCUMENTS

| | | |
|---|---|---|
| EP | 1 584 331 | 10/2005 |
| JP | 11-199854 | 7/1999 |
| JP | 2000-239649 | 9/2000 |
| JP | 2000239649 A * | 9/2000 |
| JP | 2002-226542 | 8/2002 |
| JP | 2011-21170 | 2/2011 |
| JP | 2011021170 A * | 2/2011 |

OTHER PUBLICATIONS

Document N_English Translation.*
Document O_English Translation.*
International Search Report issued Dec. 24, 2013 in International (PCT) Application No. PCT/JP2013/081670.
Translation of the Written opinion of the International Searching Authority issued Dec. 24, 2013 in International (PCT) Application No. PCT/JP2013/081670.
Extended European Search Report issued May 3, 2016 in corresponding European Application No. 13857879.4.

* cited by examiner

*Primary Examiner* — Michael L Leonard
(74) *Attorney, Agent, or Firm* — Wenderoth, Lind & Ponack, L.L.P.

(57) ABSTRACT

A urethane polymer obtained by a reaction of: a monohydroxy compound (A), a polyethylene glycol (B), a monoglyceryl ether compound (C), and an isocyanate compound (D). This urethane polymer can be used as a urethane viscosity modifier excellent in long-term storage stability, similarly to alkali thickening-type viscosity modifiers, while having characteristics similar to those of existing urethane viscosity modifiers.

3 Claims, No Drawings

URETHANE-TYPE POLYMERS AND USE THEREOF

TECHNICAL FIELD

The present invention relates to a urethane polymer and uses thereof. More particularly, the present invention relates to a urethane polymer that can be used in various fields, such as coating materials, adhesives, foodstuffs, cosmetic products, and to a urethane viscosity modifier, a urethane viscosity modifier aqueous solution, an oil-in-water emulsified composition and a cosmetic that utilize the urethane polymer.

BACKGROUND ART

Aqueous viscosity modifiers (also referred to as "thickeners") are ordinarily used in fields such as coating materials, adhesives, foodstuffs, cosmetic products and the like. By being added to various products, viscosity modifiers increase product viscosity, and make it possible to impart thereby various functions to the product. For instance, viscosity is ordinarily modified (for instance, thickening) using a viscosity modifier in oil-in-water emulsified compositions that are used in emulsions of pharmaceuticals, quasi-drugs or cosmetics. That is because modifying the viscosity elicits various effects such as improved skin application and creating a particular feel. The degree of viscosity modification varies significantly depending on the product. In some instances thickening is substantial, as in creams, while in other instances there is little change in viscosity, for instance in lotions.

Examples of generally known viscosity modifiers include, for instance, natural viscosity modifiers such as carboxymethyl cellulose, hydroxyethyl cellulose and the like; alkali thickening-type viscosity modifiers in which thickening is accomplished by an alkali, for instance polyacrylic acid or a polyacrylic acid-containing copolymer; and urethane viscosity modifiers such as urethane-modified polyethers and the like. Among the foregoing, numerous kinds of urethane viscosity modifiers are produced and used on account of various reasons. For instance, urethane viscosity modifiers allow producing various types of viscosity modifier more freely than is the case in other viscosity modifiers, and allow imparting various degrees of viscosity to products to which the viscosity modifier is added. When the product having the viscosity modifier added thereto is made into a coating film, urethane viscosity modifiers afford better water resistance in the coating film, as compared with that afforded by other viscosity modifiers, and are not readily influenced by pH (see, for instance, Patent Documents 1 to 3).

When formulated in, for instance, coating materials, existing urethane viscosity modifiers are however problematic on account of the occurrence of settling of solid components, such as pigments, contained in the coating material, due to long-term storage. The occurrence of separation of emulsion components due to long-term storage, when the viscosity modifiers are formulated in emulsions of cosmetic products, is a further problem. Such phenomena are observed also in natural viscosity modifiers such as carboxymethyl cellulose and hydroxyethyl cellulose, but are virtually not observed in alkali thickening-type viscosity modifiers, since the latter have good long-term storage stability.

In many instances, powders such as silica, titanium or the like are generally incorporated into oil-in-water emulsified compositions, in cosmetics or the like. When such powders are added to an oil-in-water emulsified composition that is thickened using a natural viscosity modifier or a urethane viscosity modifier, the powder separates immediately through precipitation or the like. Accordingly, alkali thickening-type viscosity modifiers having good stability after thickening (product stability) are generally used in order to thicken such oil-in-water emulsified compositions containing a powder.

As pointed out above, alkali thickening-type viscosity modifiers are mainly used in cosmetics and the like. However, alkali thickening-type viscosity modifiers have the drawback of being difficult to use, since they are significantly influenced by the pH of the system and by addition of salts into the system. In actual gel-like oil-in-water emulsified compositions that are obtained by using alkali thickening-type viscosity modifiers, the gel collapses easily due to changes in pH or addition of salts. A problem arises therefore in that components that can be added to gel-like oil-in-water emulsified compositions are limited, and thus alkali thickening-type viscosity modifiers cannot be used in a wide variety of applications.

Oil-in-water emulsified compositions are ordinarily produced through emulsification of water and oil-soluble components, using emulsifiers. Gel-like oil-in-water emulsified compositions that are produced using alkali thickening-type viscosity modifiers can only be produced by using surfactants (for instance, anionic surfactants or nonionic surfactants) as emulsifiers.

The use of surfactants is however undesirable in cosmetics (for instance, lotions), which must be hypoallergenic and safe towards the skin. Accordingly, many cosmetics are marketed in which no surfactant is utilized and in which the aqueous phase and the oil phase are in a separated state.

REFERENCES

Patent Documents

Patent Document 1: JP 2002-226542 A
Patent Document 2: JP 2000-239649 A
Patent Document 3: JP 11-199854 A

SUMMARY OF THE INVENTION

Problems to be Solved by the Invention

In order to solve the above problems, it is an object of the present invention to provide a novel urethane polymer that can be used as a urethane viscosity modifier of excellent long-term storage stability, similarly to alkali thickening-type viscosity modifiers, while having characteristics similar to those of existing urethane viscosity modifiers (specifically, for instance, good water resistance in a coating film when a product to which the urethane viscosity modifier has been added is made into a coating film, as well as low susceptibility to pH).

It is a further object of the present invention to provide a urethane viscosity modifier and a urethane viscosity modifier aqueous solution excellent in long-term storage stability, similarly to alkali thickening-type viscosity modifiers, while having characteristics similar to those of existing urethane viscosity modifiers.

It is yet another object of the present invention to provide an oil-in-water emulsified composition having excellent product stability and in which a powder that is added to the composition can remain dispersed stably over long periods of time, without using any surfactant as an emulsifier, and to provide a cosmetic that contains the oil-in-water emulsified composition.

Means for Solving the Problems

As a result of diligent research aimed at solving the above problems, the inventors found that a urethane polymer obtained by reacting four specific types of starting materials exhibits good characteristics as a viscosity modifier, and also as an emulsifier, and perfected the present invention on the basis of that finding.

Specifically, the present invention is a urethane polymer obtained by a reaction of:

a monohydroxy compound (A) represented by Formula (1),

wherein $R^1$ is an aliphatic hydrocarbon group having 24 to 36 carbon atoms, and m represents a number ranging from 0 to 1000;

a polyethylene glycol (B) represented by Formula (2),

wherein n represents a number ranging from 2 to 1000;
a monoglyceryl ether compound (C) represented by Formula (3),

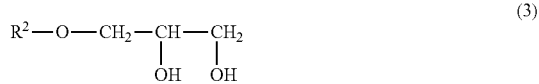

wherein $R^2$ represents an aliphatic hydrocarbon group having 5 to 12 carbon atoms; and
an isocyanate compound (D) represented by Formula (4),

wherein $R^3$ represents a hydrocarbon group having 4 to 13 carbon atoms, and q represents the number 2 or 3.

The present invention is also a urethane viscosity modifier comprising the above urethane polymer.

The present invention is also a urethane viscosity modifier aqueous solution, containing the above urethane viscosity modifier and water.

The present invention is also an oil-in-water emulsified composition containing:
the above urethane polymer (I);
a water-insoluble oil or wax-like substance (II) having a melting point of 100° C. or lower; and
water (III).

The present invention is also a cosmetic containing the above oil-in-water emulsified composition.

Effects of the Invention

The present invention succeeds in providing a novel urethane polymer that can be used as a urethane viscosity modifier of excellent long-term storage stability, similarly to alkali thickening-type viscosity modifiers, while having characteristics similar to those of existing urethane viscosity modifiers (specifically, for instance, good water resistance in a coating film when a product to which the urethane viscosity modifier has been added is made into a coating film, as well as low susceptibility to pH).

The present invention succeeds also in providing a urethane viscosity modifier and a urethane viscosity modifier aqueous solution excellent in long-term storage stability, similarly to alkali thickening-type viscosity modifiers, while having characteristics similar to those of existing urethane viscosity modifiers.

The present invention succeeds further in providing an oil-in-water emulsified composition having excellent product stability and in which a powder that is added to the composition can remain dispersed stably over long periods of time, without using any surfactant as an emulsifier, and in providing a cosmetic that contains the oil-in-water emulsified composition.

MODE FOR CARRYING OUT THE INVENTION

The urethane polymer of the present invention is obtained by reacting a monohydroxy compound (A), a polyethylene glycol (B), a monoglyceryl ether compound (C) and an isocyanate compound (D).

The monohydroxy compound (A) is represented by Formula (1).

In Formula (1), $R^1$ is a aliphatic hydrocarbon group having 24 to 36 carbon atoms. Specific examples of such aliphatic hydrocarbon groups include, for instance, alkyl groups such as tetracosyl groups, isotetracosyl groups, hexacosyl groups, isohexacosyl groups, octacosyl groups, isooctacosyl groups, triacontyl groups, isotricontyl groups, dotriacontyl groups, isodotriacontyl groups, tetratriacontyl groups, isotetratriacontyl groups, 2-decyltetradecyl groups, 2-dodecylhexadecyl groups, 2-tetradecyloctadecyl groups, 2-hexadecyloctadecyl groups and the like; and alkenyl groups such as tetracosenyl groups, isotetracosenyl groups, hexacosenyl groups, isohexacosenyl groups, octacosenyl groups, isooctacosenyl groups, triacontenyl groups, isotriacontenyl groups, dotriacontenyl groups, isodotriacontenyl groups, tetracontenyl groups, isotetracontenyl groups and the like. Among the foregoing, alkyl groups are preferred, more preferably alkyl groups having 28 to 36 carbon atoms, and yet more preferably alkyl groups having 30 to 34 carbon atoms, on account of the good functionality of the viscosity modifier that is obtained. The functionality as a viscosity modifier may be impaired, or the target product (aqueous solution or the like) may fail to be thickened, when the number of carbon atoms is smaller than 24. Moreover, functionality as a viscosity modifier is impaired when the number of carbon atoms exceeds 36.

In Formula (1), m represents a number ranging from 0 to 1000. Among the foregoing, m ranges preferably from 10 to 500, more preferably from 15 to 300, and yet more preferably from 20 to 200, since in this case good functionality as a viscosity modifier is achieved. Production time and cost become excessive if the number m exceeds 1000.

The polyethylene glycol (B) is represented by Formula (2).

In Formula (2), n denotes the average degree of polymerization, and represents a number ranging from 2 to 1000. Among the foregoing, n ranges preferably from 20 to 800, more preferably from 50 to 700, and yet more preferably from 100 to 500, since in this case good functionality as a viscosity modifier is achieved. Water solubility decreases, and functionality as a viscosity modifier is impaired, when the number n is smaller than 2. Functionality as a viscosity modifier is likewise impaired when the number n exceeds 1000.

The monoglyceryl ether compound (C) is represented by Formula (3).

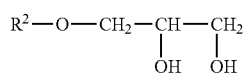
(3)

In Formula (3), R² denotes an aliphatic hydrocarbon group having 5 to 12 carbon atoms. Among the foregoing, R² is preferably an aliphatic hydrocarbon group having 6 to 10 carbon atoms. Examples of such monoglyceryl ether compounds include, for instance, monopentyl glyceryl ether, monohexyl glyceryl ether, monoheptyl glyceryl ether, monooctyl glyceryl ether, mono 2-ethylhexyl glyceryl ether, monononyl glyceryl ether, monodecyl glyceryl ether, monoundecyl glyceryl ether, monododecyl glyceryl ether and the like. The effect of long-term storage stability cannot be achieved if the number of carbon atoms is smaller than 5 or greater than 12.

The isocyanate compound (D) is represented by Formula (4).

(4)

In Formula (4), R³ represents a hydrocarbon group having 4 to 13 carbon atoms, and q represents 2 or 3. The compound is a diisocyanate compound when the value of q is 2, and a triisocyanate compound when the value of q is 3. Examples of the isocyanate compound include, for instance, aliphatic diisocyanates such as tetramethylene diisocyanate, pentamethylene diisocyanate, hexamethylene diisocyanate, 2,2-dimethyl pentane diisocyanate, 3-methoxyhexane diisocyanate, octamethylene diisocyanate, 2,2,4-trimethyl pentane diisocyanate, nonamethylene diisocyanate, decamethylene diisocyanate, 3-butoxyhexane diisocyanate, dodecamethylene diisocyanate, 4,4-biscyclohexylmethane diisocyanate and the like; aromatic diisocyanates such as metaphenylene diisocyanate, paraphenylene diisocyanate, 2,4-tolylene diisocyanate, 2,6-tolylene diisocyanate, dimethylbenzene diisocyanate, ethylbenzene diisocyanate, isopropyl benzene diisocyanate, 1,4-naphthalene diisocyanate, 1,5-naphthalene diisocyanate, 2,6-naphthalene diisocyanate, 2,7-naphthalene diisocyanate and the like; and triisocyanates such as 1-methylbenzene-2,4,6-triisocyanate, 1,3,5-trimethylbenzene-2,4,6-triisocyanate, 1,3,7-naphthalenetriisocyanate, biphenyl-2,4,4'-triisocyanate, diphenyl methane-2,4,4'-triisocyanate, 3-methyldiphenylmethane4,6,4'-triisocyanate, 1,6,11-undecanetriisocyanate, 1,8-diisocyanate-4-isocyanate methyl octane, 1,3,6-hexamethylenetriisocyanate and the like. Preferred among the foregoing are diisocyanate compounds, in that these allow for easy reaction control, low viscosity in the obtained urethane polymer, and are easy to handle. More preferably, the isocyanate compound is an aliphatic diisocyanate, from the viewpoint of achieving good functionality as a viscosity modifier. A compound having fewer than 4 carbon atoms is difficult to procure from commercially available sources, and is undesirable in industrial terms. On the other hand, water solubility decreases, and functionality as a viscosity modifier is impaired, when the number of carbon atoms exceeds 13. If the value of q is 1, the obtained compound is not a polymer, and cannot function as a viscosity modifier.

The urethane polymer of the present invention can be obtained as a result of a reaction between components (A) to (D) above. The reaction takes place through reaction of the hydroxyl groups contained in components (A), (B) and (C) and the isocyanate groups contained in component (D). Herein there are three components having hydroxyl groups, and two of these components are divalent. Accordingly, the obtained urethane polymer has a complex structure that cannot be expressed by a suitable formula.

The conditions of the reaction are not particularly limited, so long as the four components react with each other. The components may be caused to react all at once, or divisionally. Preferably, however, the compounds in (A) to (C) are mixed beforehand and the isocyanate compound (D) is added to the resulting mixture, and caused to react with the foregoing, since no reaction can take place after complete reaction of component (D) even if any one of the compounds of components (A) to (C) is then introduced into the reaction system. Specifically, compounds of (A) to (C) are introduced into the reaction system, are melt-mixed at 40 to 100° C., preferably at 60 to 80° C., and thereupon the isocyanate compound (D) is added into the reaction system, to react with compounds (A) to (C), while the above temperature is held. Thereafter, it is sufficient to hold the same temperature from 30 minutes to 3 hours, until the reaction is over.

The blending ratio of the components in the reaction is not particularly limited, but is preferably 10 to 30 moles of the monohydroxy compound (A), 5 to 20 moles of the monoglyceryl ether compound (C) and 20 to 50 moles of the isocyanate compound (D) with respect to 10 moles of the polyethylene glycol (B), and more preferably 15 to 25 moles of the monohydroxy compound (A), 8 to 15 moles of the monoglyceryl ether compound (C) and 25 to 40 moles of the isocyanate compound (D) with respect to 10 moles of the polyethylene glycol (B), since in such a case good functionality as a viscosity modifier is achieved, and the reaction is easy to control. If the blending ratio of the components deviates from the above blending ratios, some of the starting materials in the blend may remain in the system as unreacted substances, or good functionality as a viscosity modifier may fail to be achieved.

Catalysts can be used in order to accelerate the above reaction. Examples of catalysts include, for instance, strong acids such as sulfuric acid, toluenesulfonic acid and the like; metal halides such as titanium tetrachloride, hafnium chloride, zirconium chloride, aluminum chloride, gallium chloride, indium chloride, iron chloride, tin chloride, boron fluoride and the like; hydroxides, alcoholates or carbonates of alkali metals or alkaline-earth metals, for instance sodium hydroxide, potassium hydroxide, sodium methylate, sodium carbonate and the like; metal oxides such as aluminum oxide, calcium oxide, barium oxide, sodium oxide and the like; organometallic compounds such as tetraisopropyl titanate, dibutyl tin dichloride, dibutyl tin oxide, dibutyl tin bis(2-ethylhexylthioglycolate) and the like; and soaps such as sodium octylate, potassium octylate, sodium laurate, potassium laurate or the like. The blending amount of the catalyst is not particularly limited, and ranges from about 0.01 to 1 mass % with respect to the total system (total of components (A) to (D)). The reaction proceeds even without using a catalyst, but the reaction rate increases when using a catalyst, which elicits the effect of shortening the reaction time.

The urethane polymer of the present invention obtained as described above allows the viscosity of water or an aqueous solution to be adjusted by being added to the water or aqueous solution. A viscous aqueous solution or a viscous gel-like aqueous solution can be obtained by adjusting the addition amount of the urethane polymer. In particular, the viscosity adjustment effect of the urethane polymer of the present invention is little affected even by changes in the pH of the solution. When blended into a solution for forming a film, the urethane polymer of the present invention does not elicit a drop in the water resistance of the coating film that is formed out of that solution. The urethane polymer of the present invention does not suffer from the problem of settling or separation when the urethane polymer is blended, for instance, into a coating material or a cosmetic product. Accordingly, the urethane polymer of the present invention can be used as a urethane viscosity modifier excellent in long-term storage stability, similar to that of an alkali thickening-type viscosity modifier, while having characteristics similar to those of existing urethane viscosity modifiers.

Although the urethane polymer of the present invention can be used as a urethane viscosity modifier, it may also be used in the form of a urethane viscosity modifier aqueous solution. Actually, a urethane viscosity modifier made up of the urethane polymer of the present invention is ordinarily in the form of a solid, and, accordingly, it is necessary to pulverize the urethane viscosity modifier for use in a coating material, a cosmetic product or the like. Dissolving the pulverized material in a product such as a coating material, a cosmetic product or the like, however, takes a long time; accordingly, the urethane viscosity modifier is preferably used in the form of a urethane viscosity modifier aqueous solution in which the urethane viscosity modifier is diluted in a solvent such as water.

The urethane viscosity modifier aqueous solution of the present invention is explained next.

The urethane viscosity modifier aqueous solution of the present invention contains a urethane viscosity modifier made up of a urethane polymer, and water.

The water that is used in the urethane viscosity modifier aqueous solution of the present invention is not particularly limited, and pure water, RO water, deionized water, distilled water or the like can be used.

The method for preparing the urethane viscosity modifier aqueous solution of the present invention is not particularly limited, but, for instance, may involve obtaining a urethane polymer as a result of the above reaction, followed by direct addition of water or the like in the urethane polymer, and stirring the whole for about 1 to 3 hours at a temperature of about 40 to 80° C., until a homogeneous aqueous solution is obtained.

The addition amount of water is preferably such that the content of the urethane viscosity modifier in the urethane viscosity modifier aqueous solution ranges from 5 to 50 mass %, more preferably from 10 to 40 mass %. If the content of the urethane viscosity modifier is smaller than 5 mass %, the performance of a cosmetic product or the like may be adversely affected by the urethane viscosity modifier when the urethane viscosity modifier is added to the cosmetic product or the like and the addition amount of water is large, and transport and storage problems may arise. If the content of the urethane viscosity modifier exceeds 50 mass %, on the other hand, the urethane viscosity modifier may fail to dissolve completely in water, or may result in poor handleability on account of increased viscosity after dissolution.

The urethane viscosity modifier aqueous solution of the present invention may contain water and, along with water, a solvent other than water, for the purpose of promoting the dilution rate or increasing the diluted concentration. Examples of such solvents include, for instance, alcohols such as methanol, ethanol, propanol, isopropanol, butanol, ethylene glycol, propylene glycol, 1,2-butanediol, 1,3-butanediol and the like; and polyether-based solvents resulting from adding 1 to 10 moles of ethylene oxide and/or propylene oxide to an alcohol having a hydrocarbon groups that has 1 to 10 carbon atoms. Polyether-based solvents are preferred among the foregoing, in that they do not give rise to, for instance, foul odors when evaporating, and afford a high viscosity-lowering effect. More preferred are polyether-based solvents resulting from adding 3 to 10 moles of ethylene oxide to a monohydric alcohol that has an alkyl group with 5 to 10 carbon atoms. The content of the solvent in the urethane viscosity modifier aqueous solution ranges preferably from 3 to 20 mass %, more preferably from 5 to 15 mass %.

From the viewpoint of imparting various characteristics, the urethane viscosity modifier aqueous solution of the present invention may further contain known additives in the technical field in question, so long as the effect of the present invention is not impaired thereby.

In addition to having excellent long-term storage stability similar to alkali thickening-type viscosity modifiers, while having characteristics similar to those of existing urethane viscosity modifiers, the urethane viscosity modifier aqueous solution of the present invention dissolves easily in various products such as coating materials and cosmetic products. Accordingly, the urethane viscosity modifier aqueous solution of the present invention can be readily used in various products.

The urethane viscosity modifier of the present invention and the urethane viscosity modifier aqueous solution can be used in any product so long as the foregoing are used to adjust the viscosity of an aqueous solution. Examples of such products include, for instance, aqueous coating materials, aqueous adhesives, aqueous cleaning agents, cosmetic products and the like. Preferred among the foregoing are creams, essences, lotions, emulsions and liquid foundations from which long-term storage stability is strongly required.

The addition amount of the urethane viscosity modifier and the urethane viscosity modifier aqueous solution of the present invention in various products may be such that, preferably, the urethane viscosity modifier is 0.01 to 10 mass %, more preferably 0.03 to 5 mass %, and yet more preferably 0.05 to 3 mass % of the total system (given product plus the urethane viscosity modifier or urethane viscosity modifier aqueous solution of the present invention). The urethane viscosity modifier may fail to function sufficiently as a viscosity modifier if the addition amount is such that the urethane viscosity modifier is less than 0.1 mass %. On the other hand, the urethane viscosity modifier may fail to dissolve completely in various products if the addition amount is such that the urethane viscosity modifier exceeds 10 mass %.

The urethane polymer of the present invention has not only good characteristics as a viscosity modifier, but also good characteristics as an emulsifier. As a result, it becomes possible to obtain an oil-in-water emulsified composition having excellent product stability and in which a powder that is added to the composition can remain dispersed stably over long periods of time, without using any surfactant as an emulsifier, by combining the urethane polymer of the present invention with a specific water-insoluble oil or wax-like substance and water.

The oil-in-water emulsified composition of the present invention is explained next.

The oil-in-water emulsified composition of the present invention contains the urethane polymer (I) explained above, an oil or wax-like substance (II), and water (III).

The oil or wax-like substance (II) that is used in the oil-in-water emulsified composition of the present invention need only form an emulsion when mixed with water (III), and is not particularly limited so long as it is a water-insoluble oil or wax-like substance (II) that has a melting point of 100° C. or lower. The oil or wax-like substance (II) cannot form an emulsion when mixed with water (III) if the melting point of the oil or wax-like substance (II) exceeds 100° C. and/or the oil or wax-like substance (II) is water-soluble.

The term "water-insoluble" as used in the present description denotes a solubility of 3 g/100 g or less (solubility of 3 g or less with respect to 100 g of water), and preferably a solubility of 1 g/100 g or less, in water at 25° C.

Examples of the oil or wax-like substance (II) having such characteristics include, for instance, higher alcohols such as cetyl alcohol, isostearyl alcohol, lauryl alcohol, hexadecyl alcohol, octyldodecanol and the like; fatty acids such as isostearic acid, undecylenic acid, oleic acid and the like;

esters such as myristyl myristate, hexyl laurate, decyl oleate, isopropyl myristate, hexyldecyl dimethyloctanoate, glyceryl monostearate, diethyl phthalate, ethylene glycol monostearate, octyl oxystearate and the like; hydrocarbons such as liquid paraffin, vaseline, squalane and the like; waxes such as lanolin, reduced lanolin, carnauba wax and the like; oils and fats such as avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, Chinese tung oil, Japanese tung oil, jojoba oil, germ oil and the like; synthetic oils such as ethylene-α-olefin co-oligomers and the like; silicone compounds such as dimethyl polysiloxane, methylhydrogenpolysiloxane, methylphenyl polysiloxane, polyether-modified organopolysiloxanes, fluoroalkyl-polyoxyalkylene co-modified organopolysiloxanes, alkyl-modified organopolysiloxanes, terminal-modified organopolysiloxanes, fluorine-modified organopolysiloxanes, amodimethicone, amino-modified organopolysiloxanes, silicone gel, acrylic silicone, trimethylsiloxy silicate and the like; and fluorine compound such as perfluoropolyethers, fluorinated pitches, fluorocarbons, fluoroalcohols and the like. Preferred among the foregoing are higher alcohols, esters, hydrocarbons and oils or fats, on account of their high frequency of use in cosmetics. These components can be used singly or in combinations of two or more types. Components having a melting point in excess of 100° C. can be used provided that, when used in a combination of two or more types, the resulting melting point is not higher than 100° C.

The water (III) that is used in the oil-in-water emulsified composition of the present invention is not particularly limited, and may be pure water, RO water, deionized water, distilled water or the like.

The oil-in-water emulsified composition of the present invention can be produced in accordance with any known method, using the urethane polymer (I), the oil or wax-like substance (II) and the water (III). For instance, the oil-in-water emulsified composition of the present invention can be produced by charging the urethane polymer (I), the oil or wax-like substance (II) and the water (III) into a vessel, followed by mixing for a given lapse of time using mixing equipment such as a stirrer or a homomixer.

During mixing, the oil or wax-like substance (II) and the water (III) can be emulsified by the urethane polymer (I), since the latter functions similarly to an emulsifier. Further, the viscosity and form (viscous liquid or gel-like) of the oil-in-water emulsified composition can be modified depending on the blending amount of the urethane polymer (I), by virtue of the function of the latter as a viscosity modifier.

The blending ratio of the components is not particularly limited, and it suffices that the ratio be adjusted in accordance with the use of the oil-in-water emulsified composition. However, the urethane polymer (I) ranges preferably from 0.1 to 10 parts by mass, more preferably from 0.3 to 5 parts by mass, and water (III) ranges preferably from 40 to 80,000 parts by mass, more preferably 100 to 10,000 parts by mass, with respect to 100 parts by mass of the oil or wax-like substance (II). The functionality of the urethane polymer (I) as an emulsifier may fail to be sufficiently brought out when the blending ratio of the urethane polymer (I) is smaller than 0.1 part by mass. On the other hand, an insoluble fraction may remain, or an effect commensurate with the addition amount may fail to be obtained, if the content of urethane polymer (I) exceeds 10 parts by mass. The oil-in-water emulsified composition may be difficult to form if the content of water (III) is smaller than 40 parts by mass. On the other hand, the content of oil or wax-like substance (II) decreases, and emulsification may fail, if the content of water (III) exceeds 80,000 parts by mass.

From the viewpoint of enhancing product stability, the oil-in-water emulsified composition of the present invention can further contain an alcohol (IV) represented by Formula (5) below, besides components (I) to (III). Addition of the alcohol (IV) results in increased product stability of the oil-in-water emulsified composition of the present invention itself, and affords a more pronounced effect of suppressing separating or settling of insoluble matter, for instance powder, when such insoluble matter is added to the oil-in-water emulsified composition of the present invention.

$$R^4\text{---}[\text{---OH}]_p \quad (5)$$

In Formula (5), $R^4$ represents a hydrocarbon group having 2 to 8 carbon atoms, preferably a hydrocarbon group having 3 to 7 carbon atoms, or a hydrocarbon group having 2 to 8 carbon atoms and comprising one or more ether bonds, and p represents a number from 1 to 6. The product stability of the oil-in-water emulsified composition cannot be enhanced if the number of carbon atoms of the hydrocarbon group is smaller than 2 or greater than 8. Similarly, the product stability of the oil-in-water emulsified composition cannot be enhanced if p exceeds 6. Examples of hydrocarbon groups having 2 to 8 carbon atoms include, for instance, ethylene groups, propylene groups, butylene groups, pentylene groups, hexylene groups, heptylene groups, phenylene groups, methyl phenylene groups and the like.

Examples of the alcohol (IV) include, for instance, monohydric alcohols such as ethanol, propanol, isopropanol and the like; dihydric alcohols such as ethylene glycol, 1,2-propylene glycol, 1,3-propylene glycol, 1,2-butylene glycol, 1,3-butylene glycol, 1,4-butylene glycol, 1,2-pentanediol, 1,3-pentanediol, 1,4-pentanediol, 1,5-pentanediol, 1,2-hexanediol, 1,3-hexanediol, 1,6-hexanediol, 1,2-heptanediol, 1,7-heptanediol, 1,2-octanediol, 1,8-octanediol, dihydroxybenzene and the like; trihydric alcohols such as glycerin, trimethylol propane and the like; polyhydric alcohols such as diglycerol, pentaerythritol, monosaccharides and the like; and ethylene oxide adducts and propylene oxide adducts of the foregoing alcohols. The alcohols can be used singly or in combinations of two or more types.

Even among the alcohol (IV), in terms of stably eliciting the above effect stably, dihydric or trihydric alcohols having 2 to 7 carbon atoms are preferred, dihydric alcohols having 3 to 5 carbon atoms are more preferable, and dihydric alcohols having 4 carbon atoms are yet more preferable.

The addition amount of the alcohol (IV) is not particularly limited, and it suffices that the amount be adjusted in accordance with the use of the oil-in-water emulsified composition, but, preferably, the addition amount of the alcohol (IV) ranges from 1 to 30 parts by mass, more preferably 1 to 10 parts by mass, with respect to 100 parts by mass of the oil or wax-like substance (II). Product stability cannot be enhanced sufficiently if the addition amount of the alcohol (IV) is smaller than 1 part by mass. On the other hand, an effect commensurate with the addition amount may fail to be obtained, if the addition amount of the alcohol (IV) exceeds 30 parts by mass.

The method of addition of the alcohol (IV) is not particularly limited, but for instance a method can be resorted to wherein the alcohol (IV) is added together with the urethane polymer (I), the oil or wax-like substance (II) and the water (III), and the foregoing are mixed, or a method wherein the urethane polymer (I), the oil or wax-like substance (II) and the water (III) are mixed, and thereafter the alcohol (IV) is added separately, whereupon the whole is mixed.

The oil-in-water emulsified composition of the present invention can contain a powder, from the viewpoint of imparting various effects (for instance, coloring) to the oil-in-water emulsified composition. Even if a powder is added to the oil-in-water emulsified composition of the present invention, separation and settling of the powder are suppressed, and the powder can be dispersed stably in the oil-in-water emulsified composition over long periods of time.

The powder is not particularly limited, and may be sparingly soluble or insoluble in oils or the wax-like substance (II) and water (III). Examples of the powder include, for instance, inorganic powders (for instance talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstate salts, magnesium, silica, zeolites, barium sulfate, calcined calcium sulfate (calcined gypsum), calcium phosphate, fluorapatite, hydroxyapatite, ceramic powders, metal soaps (for example, zinc myristate, calcium palmitate, aluminum stearate), boron nitride and the like); organic powders (for example, polyamide resin powders (nylon powder), polyethylene powders, polymethyl methacrylate powders, polystyrene powders, styrene-acrylic acid copolymer resin powders, benzoguanamine resin powders, polytetrafluoroethylene powders, cellulose powders and the like); inorganic white pigments (for instance, titanium dioxide, zinc oxide and the like); inorganic red pigments (for instance, iron oxide (red iron oxide), iron titanate and the like); inorganic brown pigments (for instance, γ-iron oxide and the like); inorganic yellow pigments (for instance, yellow iron oxide, ocher and the like); inorganic black pigments (for instance, black iron oxide, titanium suboxide and the like); inorganic violet pigments (for instance, manganese violet, cobalt violet and the like); inorganic green pigments (for instance, chromium oxide, chromium hydroxide, cobalt titanate and the like); inorganic blue pigments (for instance, ultramarine blue, prussian blue and the like); and pearl pigments (for instance, titanium oxide-coated mica, titanium oxide-coated bismuth oxychloride, titanium oxide-coated talc, colored titanium oxide-coated mica, bismuth oxychloride, fish scale foil and the like); as well as metal powder pigments (for instance, aluminum powder, copper powder). The foregoing can be used singly or in combinations of two or more types. The addition amount of the powder is not particularly limited, so long as the effect of the present invention is not impaired, but preferably the addition amount of the powder ranges from 0.1 to 100 parts by mass, more preferably 1 to 80 parts by mass, with respect to 100 parts by mass of the total amount of the oil or wax-like substance (II) plus water (III).

In addition to the above components, one, two or more types of various components that are used depending on various types of application (for instance, humectants, metal-ion sequestering agents, lower alcohols, polyhydric alcohols, sugars, amino acids, organic amines, pH adjusting agents, skin nutrients, vitamins, antioxidants and the like) may also be blended, as needed, into the oil-in-water emulsified composition of the present invention. The blending amount of these components is not particularly limited, so long as the effect of the present invention is not impaired.

The oil-in-water emulsified composition of the present invention is excellent in product stability, such that a powder that is added to the oil-in-water emulsified composition can remain dispersed therein stably over long periods of time, without the use of a surfactant as an emulsifier. As a result, the oil-in-water emulsified composition can be used in various applications. In particular, the oil-in-water emulsified composition of the present invention is preferably used in cosmetics or quasi-drugs, and more preferably in cosmetics, since the composition uses no surfactants and is hypoallergenic towards the skin.

Therefore, the cosmetic of the present invention comprises the oil-in-water emulsified composition applied above.

Examples of the cosmetic that can be used include creams, face-cleansing creams, cleansing foams, cleansing creams, cleansing milks, cleansing lotions, massage creams, moisture creams, sunscreen creams, hair liquids, setting lotions, hair bleaches, color rinses, permanent-wave liquids, hand creams, lipsticks, liquid foundations, lotions, cosmetic liquids, milky lotions, eau de cologne, nail cosmetics, mascara, eyeliners, shampoos, rinses, treatments, body soaps and the like.

EXAMPLES

The present invention will be explained next in further detail on the basis of working examples and comparative examples. However, the present invention is not limited to these examples.

<Synthesis of Urethane Polymers>
(Starting Materials Used)
A-1: 50-EO adduct of an alcohol having 32 carbon atoms (2-tetradecyloctadecanol)
A-2: 250-EO adduct of an alcohol having 32 carbon atoms (2-tetradecyloctadecanol)
A-3: 150-EO adduct of an alcohol having 28 carbon atoms (2-dodecylhexadecanol)
A-4: 150-EO adduct of an alcohol having 24 carbon atoms (2-decyltetradecyl)
B-1: polyoxyethylene glycol having a weight-average molecular weight of 11000
B-2: polyoxyethylene glycol having a weight-average molecular weight of 8000
C-1: 2-ethylhexyl glyceryl ether
C-2: monododecyl glyceryl ether
D-1: hexamethylene diisocyanate
D-2: metaphenylene diisocyanate
A'-1: 150-EO adduct of a C22 alcohol (2-decyldodecyl)
C'-1: butyl glyceryl ether
*EO adduct: ethylene oxide adduct
(Synthesis Method)
[Synthesis of Inventive Product 1]

A four-necked flask having a capacity of capacity 2000 mL and equipped with a thermometer, a nitrogen introduction tube and a stirrer, was charged with 267 g (0.1 moles) of A-1, 550 g (0.05 moles) of B-1 and 10.2 g (0.05 moles) of C-1. The interior of the system was purged with nitrogen, after which the temperature was raised to 80 to 90° C., to melt the charge, with mixing until homogeneity. After verifying that all components were homogeneously mixed, 25 g (0.15 moles) of D-1 were added into the system, and the system was left to react at the same temperature for 3 hours, to yield Inventive product 1.

[Synthesis of Inventive Products 2 to 9]

Inventive products 2 to 9 were obtained through synthesis under conditions identical to those of the synthesis of Inventive product 1, but herein the starting materials and/or blending proportions thereof were modified as given in Table 1.

[Synthesis of Comparative Products 1 to 5]

Comparative products 1 to 5 were obtained through synthesis under conditions identical to those of the synthesis of Inventive product 1, but herein the starting materials and/or blending proportions thereof were modified as given in Table 1.

[Comparative Products 6 to 8]

Commercially available viscosity modifiers were used as Comparative products 6 to 8.

Comparative product 6: hydroxymethyl cellulose (trade name: HEC, by Sumitomo Seika Chemicals Co. Ltd.)

Comparative product 7: methyl cellulose (trade name: Mecellose MC, by Tomoe Engineering Co., Ltd.)

Comparative product 8: carboxyvinyl polymer (trade name: Carbopol 980, by The Lubrizol Corporation)

TABLE 1

|  | Inventive products | | | | | | | | | Comparative products | | | | |
| --- | --- | --- | --- | --- | --- | --- | --- | --- | --- | --- | --- | --- | --- | --- |
|  | 1 | 2 | 3 | 4 | 5 | 6 | 7 | 8 | 9 | 1 | 2 | 3 | 4 | 5 |
| A-1 | 0.1 | — | — | — | 0.1 | 0.1 | 0.1 | 0.1 | 0.1 | 0.1 | — | 0.1 | 0.1 | — |
| A-2 | — | 0.1 | — | — | — | — | — | — | — | — | 0.1 | — | — | — |
| A-3 | — | — | 0.1 | — | — | — | — | — | — | — | — | — | — | — |
| A-4 | — | — | — | 0.1 | — | — | — | — | — | — | — | — | — | — |
| B-1 | 0.05 | 0.05 | 0.05 | 0.05 | — | 0.05 | 0.05 | 0.05 | 0.05 | 0.05 | 0.05 | — | 0.05 | 0.05 |
| B-2 | — | — | — | — | 0.05 | — | — | — | — | — | — | — | — | — |
| C-1 | 0.05 | 0.05 | — | 0.05 | 0.05 | 0.05 | 0.03 | 0.1 | 0.01 | — | — | — | — | 0.05 |
| C-2 | — | — | 0.05 | — | — | — | — | — | — | — | — | — | — | — |
| D-1 | 0.15 | 0.15 | 0.15 | 0.15 | 0.15 | — | 0.15 | 0.15 | 0.15 | 0.15 | 0.1 | 0.05 | 0.15 | 0.15 |
| D-2 | — | — | — | — | — | 0.15 | — | — | — | — | — | — | — | — |
| A'-1 | — | — | — | — | — | — | — | — | — | — | — | — | — | 0.1 |
| C'-1 | — | — | — | — | — | — | — | — | — | — | — | 0.05 | — | — |

(Remarks)
The numerical value units in the table are moles.

Example 1: Viscosity Test

Inventive products 1 to 9 and Comparative products 1 to 8 were added to pure water, to a proportion of 1.5 mass %, and after complete dissolution, the storage modulus (G') and loss modulus (G") at a respective angular frequency (w), using a rheometer (viscoelasticity measuring device) were measured. The results are given in Table 2. Herein, G' denotes the capability (elastic component) of maintaining the stress that is stored inside the measurement liquid, while G" denotes the viscosity component for which energy that is imparted to the measurement liquid was dissipated in the form of heat. If G' is higher than G", the liquid has elastic properties (solid properties), and, accordingly, settling and separation of components within the liquid are unlikelier to occur. A constant difference between G' and G" denotes a viscous body behavior that is identical at all frequencies. The rheometer and measurement conditions are as follows.

Equipment Used
Equipment name: MCR301 (by Anton Paar GmbH)
Measurement Conditions
Measurement fixture: PP50 (parallel plate, φ50 mm)
Measurement position: 0.5 mm (distance from stage to parallel plate)
Strain (deflection angle): 5%
Measurement temperature: 25° C.

TABLE 2

|  |  |  | Angular frequency (rad/s) | | | | | | | |
| --- | --- | --- | --- | --- | --- | --- | --- | --- | --- | --- |
|  |  |  | 0.1 | 0.5 | 1 | 5 | 10 | 20 | 50 | 100 |
| Inventive products | 1 | G' | 110 | 112 | 113 | 115 | 117 | 119 | 122 | 127 |
|  |  | G" | 5 | 4 | 4 | 5 | 6 | 6 | 7 | 8 |
|  | 2 | G' | 140 | 145 | 146 | 148 | 150 | 151 | 149 | 145 |
|  |  | G" | 17 | 17 | 16 | 16 | 16 | 15 | 15 | 16 |
|  | 3 | G' | 160 | 172 | 174 | 176 | 175 | 175 | 173 | 172 |
|  |  | G" | 57 | 22 | 17 | 17 | 16 | 16 | 15 | 15 |
|  | 4 | G' | 121 | 126 | 137 | 137 | 138 | 138 | 140 | 142 |
|  |  | G" | 62 | 45 | 32 | 29 | 29 | 27 | 26 | 24 |
|  | 5 | G' | 105 | 106 | 107 | 107 | 108 | 110 | 111 | 113 |
|  |  | G" | 4 | 3 | 3 | 4 | 5 | 5 | 5 | 6 |
|  | 6 | G' | 132 | 135 | 136 | 137 | 139 | 140 | 142 | 145 |
|  |  | G" | 23 | 18 | 15 | 15 | 15 | 14 | 13 | 12 |
|  | 7 | G' | 116 | 120 | 121 | 123 | 125 | 126 | 128 | 130 |
|  |  | G" | 21 | 15 | 14 | 13 | 13 | 12 | 12 | 13 |
|  | 8 | G' | 124 | 126 | 127 | 127 | 129 | 130 | 131 | 133 |
|  |  | G" | 26 | 20 | 18 | 17 | 17 | 16 | 16 | 16 |
|  | 9 | G' | 115 | 119 | 120 | 121 | 121 | 123 | 124 | 126 |
|  |  | G" | 58 | 43 | 21 | 21 | 20 | 19 | 18 | 19 |
| Comparative products | 1 | G' | 27 | 95 | 116 | 122 | 112 | 83 | 75 | 74 |
|  |  | G" | 48 | 47 | 26 | 8 | 6 | 5 | 4 | 4 |
|  | 2 | G' | 16 | 68 | 102 | 108 | 104 | 93 | 87 | 81 |
|  |  | G" | 43 | 40 | 21 | 7 | 7 | 5 | 4 | 4 |
|  | 3 | G' | — | — | — | — | — | — | — | — |
|  |  | G" | — | — | — | — | — | — | — | — |
|  | 4 | G' | 33 | 99 | 120 | 124 | 125 | 120 | 115 | 109 |
|  |  | G" | 45 | 13 | 13 | 12 | 12 | 11 | 11 | 10 |
|  | 5 | G' | — | — | — | — | — | — | — | — |
|  |  | G" | — | — | — | — | — | — | — | — |
|  | 6 | G' | 1.5 | 4.1 | 9.6 | 33 | 69 | 102 | 134 | 168 |
|  |  | G" | 3.6 | 1.1 | 2.2 | 55 | 90 | 121 | 145 | 191 |
|  | 7 | G' | 1.7 | 5.9 | 11 | 25 | 34 | 38 | 49 | 63 |
|  |  | G" | 3.7 | 8.3 | 12 | 21 | 26 | 29 | 35 | 42 |

TABLE 2-continued

| | | Angular frequency (rad/s) | | | | | | | |
|---|---|---|---|---|---|---|---|---|---|
| | | 0.1 | 0.5 | 1 | 5 | 10 | 20 | 50 | 100 |
| 8 | G' | 312 | 326 | 351 | 364 | 380 | 385 | 391 | 397 |
| | G" | 18 | 16 | 26 | 34 | 39 | 43 | 46 | 50 |

(Remarks)
The units of G' and G" are Pa.
Comparative product 3 did not dissolve in water, and could not be tested.
Comparative product 5 failed to thicken an aqueous solution, and hence could not be tested.

As Table 2 indicates, some of the inventive products exhibited a small difference between G' and G" at a region of low angular frequency, but G' took on a larger value than G" in all instances. This is thought to make the occurrence of component settling and/or separation in the liquid unlikely.

By contrast, the comparative products exhibit angular frequency regions in which G' is smaller than G", with the exception of Comparative product 8. This is thought to make the occurrence of component settling and/or separation in the liquid likelier. In Comparative product 8, component settling and/or separation in the liquid does not occur readily, but an alkali thickener (sodium polyacrylate) is involved herein, and hence the comparative product is difficult to use without being influenced by pH.

Example 2: Stability Test

Respective gels were produced by dissolving the viscosity modifiers of Inventive products 1 to 9 and Comparative products 1 to 2, 4 and 6 to 8 in pure water, to a proportion of 1 mass %. Thereafter, a titanium oxide powder was added to each of the produced gels, to a proportion of 5 mass %, and the whole was stirred of 1 hour in a stirrer, until homogeneity. Each gel having titanium oxide homogeneously dispersed therein was left to stand in a thermostatic bath at 25° C., and the behavior of the titanium oxide was observed visually. The results are given in Table 3.

TABLE 3

| | Inventive products | | | | | | | | | Comparative products | | | | | |
|---|---|---|---|---|---|---|---|---|---|---|---|---|---|---|---|
| | 1 | 2 | 3 | 4 | 5 | 6 | 7 | 8 | 9 | 1 | 2 | 4 | 6 | 7 | 8 |
| Result | ○ | ○ | ○ | ○ | ○ | ○ | ○ | ○ | ○ | Δ | Δ | Δ | X | X | ○ |

(Remarks)
○ = No change in appearance after 4 weeks
Δ = Separation or settling at 3 days to 1 week
X = Separation or settling in less than 3 day As Table 3 reveals, the appearance of Inventive products 1 to 9 and Comparative product 8 did not change even after four weeks, which was indicative of good storage stability of the dispersed solid. By contrast, separation or precipitation of titanium oxide, in a lapse of time from three days to one week, was observed in Comparative products 1, 2 and 4. Separation or precipitation of titanium oxide in fewer than three days was observed in Comparative products 6 and 7. These results are identical to the results of the viscosity test (Example 1) measured mechanically.

As the above results reveal, the present invention succeeds in providing a novel urethane polymer that can be used as a urethane viscosity modifier with excellent long-term storage stability, similarly to alkali thickening-type viscosity modifiers, while having characteristics similar to those of existing urethane viscosity modifiers (specifically, for instance, good water resistance in a coating film when a product to which the urethane viscosity modifier has been added is made into a coating film, as well as low susceptibility to pH) The present invention also succeed also in providing a urethane viscosity modifier and a urethane viscosity modifier aqueous solution excellent in long-term storage stability, similarly to alkali thickening-type viscosity modifiers, while having characteristics similar to those of existing urethane viscosity modifiers.

<Synthesis of Urethane Polymers>
(Starting Materials Used)
a-1: 50-EO adduct of an alcohol having 32 carbon atoms (2-tetradecyloctadecanol)
a-2: 150-EO adduct of an alcohol having 24 carbon atoms (2-decyltetradecyl)
b-1: polyoxyethylene glycol having a weight-average molecular weight of 11000
c-1: monooctyl glyceryl ether
c-2: monododecyl glyceryl ether
d-1: hexamethylene diisocyanate
d-2: metaphenylene diisocyanate
a'-1: 150-EO adduct of a C22 alcohol (2-decyldodecyl)
c'-1: butyl glyceryl ether
*EO adduct: ethylene oxide adduct
(Synthesis Method)
A four-necked flask having a capacity of capacity 2000 mL and equipped with a thermometer, a nitrogen introduction tube and a stirrer, was charged with 267 g (0.1 moles) of starting material (a-1), 550 g (0.05 moles) of starting material (b-1) and 10.2 g (0.05 moles) of starting material (c-1). The interior of the system was purged with nitrogen, after which the temperature was raised to 80 to 90° C., to melt the charge, with mixing until homogeneity. After verifying that all components were homogeneously mixed, 25 g (0.15 moles) of starting material (d-1) were added into the system, and the system was left to react at the same temperature for 3 hours, to yield a urethane polymer (I-1).

Urethane polymers (I-2) to (I-6) were obtained through synthesis under conditions identical to those of the synthesis of the urethane polymer (I-1), but herein the starting materials and/or blending proportions thereof were modified as given in Table 4. The units of the blending proportion in Table 4 are moles.

TABLE 4

| Starting material | Urethane-type polymers | | | | | |
|---|---|---|---|---|---|---|
| | I-1 | I-2 | I-3 | I-4 | I-5 | I-6 |
| a-1 | 0.1 | — | 0.1 | — | 0.1 | 0.1 |
| a-2 | — | 0.1 | — | 0.1 | — | — |
| b-1 | 0.05 | 0.05 | 0.05 | 0.05 | 0.05 | 0.05 |
| c-1 | 0.05 | 0.05 | — | — | 0.02 | 0.05 |
| c-2 | — | — | 0.05 | 0.05 | 0.03 | — |
| d-1 | 0.15 | 0.15 | 0.15 | 0.15 | 0.15 | — |
| d-2 | — | — | — | — | — | 0.15 |

Urethane polymers for comparison (I'-1) to (I'-5) were obtained through synthesis under conditions identical to those of the synthesis of the urethane polymer (I-1), but herein the starting materials and/or blending proportions thereof were modified as given in Table 5. The units of the blending proportion in Table 5 are moles.

TABLE 5

| Starting material | Urethane-type polymers for comparison | | | | |
|---|---|---|---|---|---|
| | I'-1 | I'-2 | I'-3 | I'-4 | I'-5 |
| a-1 | 0.1 | — | 0.1 | 0.1 | — |
| a-2 | — | 0.1 | — | — | — |
| b-1 | 0.05 | 0.05 | — | 0.05 | 0.05 |
| c-1 | — | — | — | — | 0.05 |
| d-1 | 0.15 | 0.1 | 0_05 | 0.15 | 0.15 |
| a'-1 | — | — | — | — | 0.1 |
| c'-1 | — | — | — | 0.05 | — |

<Preparation of Oil-in-Water Emulsified Compositions>
(Starting Materials Used)
I-1 to I-6: synthesized urethane polymers above
I'-1 to I'-5: synthesized urethane polymers for comparison above
I'-6: hydroxymethyl cellulose (trade name: HEC, by Sumitomo Seika Chemicals Co. Ltd.)
I'-7: methyl cellulose (trade name: Mecellose MC, by Tomoe Engineering Co., Ltd.)
I'-8: carboxyvinyl polymer (trade name: Carbopol 980, by The Lubrizol Corporation)
Note) I'-6 to I'-8 are commercially available viscosity modifiers.
II-1: liquid paraffin (0.85 to 0.89 g/ml (20° C.), by Wako Pure Chemical Industries)
II-2: olive oil
III: water
IV-1: 1,2-propylene glycol
IV-2: 1,3-butanediol
IV-3: 1,2-hexanediol
(Preparation Method)
Herein, starting material (III) and starting material (I-1) were charged into a 1000 mL beaker, which was then heated at 50° C. until starting material (I-1) had dissolved completely. Thereafter, starting material (II-1) was added while under stirring at the same temperature. Once addition was over, the whole was stirred continuously for 10 minutes, to yield thereby an oil-in-water emulsified composition (Inventive product 10). The blending proportions (mass %) of the various starting materials were as given in Table 6 below, so as to yield a total 500 g of the oil-in-water emulsified composition.

Oil-in-water emulsified compositions (Inventive products 11 to 20) were obtained by being prepared in accordance with the same preparation method as that of the oil-in-water emulsified composition of Inventive product 10, but herein the starting materials and/or blending proportions thereof were modified as given in Table 6.

TABLE 6

| | Inventive products | | | | | | | | | | |
|---|---|---|---|---|---|---|---|---|---|---|---|
| | 10 | 11 | 12 | 13 | 14 | 15 | 16 | 17 | 18 | 19 | 20 |
| I-1 | 1 | — | — | — | — | — | 1 | 0.5 | 1 | 1 | 1 |
| I-2 | — | 1 | — | — | — | — | — | — | — | — | — |
| I-3 | — | — | 1 | — | — | — | — | — | — | — | — |
| I-4 | — | — | — | 1 | — | — | — | — | — | — | — |
| I-5 | — | — | — | — | 1 | — | — | — | — | — | — |
| I-6 | — | — | — | — | — | 1 | — | — | — | — | — |
| II-1 | 30 | 30 | 30 | 30 | 30 | 30 | — | — | 30 | 30 | 30 |
| II-2 | — | — | — | — | — | — | 30 | 70 | — | — | — |
| III | 69 | 69 | 69 | 69 | 69 | 69 | 69 | 29.5 | 64 | 64 | 64 |
| IV-1 | — | — | — | — | — | — | — | — | 5 | — | — |
| IV-2 | — | — | — | — | — | — | — | — | — | 5 | — |
| IV-3 | — | — | — | — | — | — | — | — | — | — | 5 |

Oil-in-water emulsified compositions (Comparative products 9 to 19) were obtained by being prepared in accordance with the same preparation method as that of the oil-in-water emulsified composition of Inventive product 10, but herein the starting materials and/or blending proportions thereof were modified as given in Table 7.

TABLE 7

| | Comparative products | | | | | | | | | | |
|---|---|---|---|---|---|---|---|---|---|---|---|
| | 9 | 10 | 11 | 12 | 13 | 14 | 15 | 16 | 17 | 18 | 19 |
| I-1 | 1 | — | — | — | — | — | — | — | — | — | — |
| I-2 | — | 1 | — | — | — | — | — | — | 1 | — | — |
| I-3 | — | — | 1 | — | — | — | — | — | — | — | — |
| I-4 | — | — | — | 1 | — | — | — | — | — | — | — |
| I-5 | — | — | — | — | 1 | — | — | — | — | — | — |
| I-6 | — | — | — | — | — | 1 | — | — | — | 1 | — |
| I-7 | — | — | — | — | — | — | 1 | — | — | — | — |
| I-8 | — | — | — | — | — | — | — | 1 | — | — | 1 |
| II-1 | 30 | 30 | 30 | 30 | 30 | 30 | 30 | 30 | 30 | 30 | 30 |
| III | 69 | 69 | 69 | 69 | 69 | 69 | 69 | 69 | 64 | 64 | 64 |
| IV-2 | — | — | — | — | — | — | — | — | 5 | 5 | 5 |

Example 3: Evaluation of the Stability of Oil-in-Water Emulsified Compositions

The prepared oil-in-water emulsified compositions of the above inventive products and comparative products were sealed in 100 mL screw tubes, and were left to stand in a thermostatic bath at 25° C. The state of each oil-in-water emulsified composition one hour, one week, one month, two months, three months and four months after having been set in the thermostatic bath was observed visually, and was evaluated in accordance with the below-described criteria.

○: no change in the emulsified state

Δ: transparent oil phase slightly appreciable at the top of the oil-in-water emulsified composition x: complete separation of aqueous phase and oil phase The evaluation results are given in Table 8. Instances of complete separation between the aqueous phase and the oil phase (rating x) were not further evaluated thereafter.

TABLE 8

| | Evaluation results for stability | | | | | |
|---|---|---|---|---|---|---|
| | 1 hour | 1 week | 1 month | 2 months | 3 months | 4 months |
| Inventive product 10 | ○ | ○ | ○ | ○ | Δ | X |
| Inventive product 11 | ○ | ○ | ○ | ○ | Δ | X |
| Inventive product 12 | ○ | ○ | ○ | ○ | Δ | X |
| Inventive product 13 | ○ | ○ | ○ | ○ | Δ | X |
| Inventive product 14 | ○ | ○ | ○ | ○ | Δ | X |
| Inventive product 15 | ○ | ○ | ○ | ○ | Δ | X |
| Inventive product 16 | ○ | ○ | ○ | ○ | Δ | X |
| Inventive product 17 | ○ | ○ | ○ | ○ | Δ | X |
| Inventive product 18 | ○ | ○ | ○ | ○ | ○ | Δ |
| Inventive product 19 | ○ | ○ | ○ | ○ | ○ | ○ |
| Inventive product 20 | ○ | ○ | ○ | ○ | ○ | Δ |
| Comparative product 9 | ○ | ○ | Δ | X | — | — |
| Comparative product 10 | ○ | ○ | Δ | X | — | — |
| Comparative product 11 | ○ | ○ | Δ | X | — | — |
| Comparative product 12 | ○ | ○ | Δ | X | — | — |
| Comparative product 13 | ○ | ○ | Δ | X | — | — |
| Comparative product 14 | X | — | — | — | — | — |
| Comparative product 15 | X | — | — | — | — | — |
| Comparative product 16 | X | — | — | — | — | — |
| Comparative product 17 | ○ | ○ | Δ | X | — | — |
| Comparative product 18 | X | — | — | — | — | — |
| Comparative product 19 | X | — | — | — | — | — |

As the results of Table 8 indicate, the oil-in-water emulsified compositions of inventive products exhibit superior stability, in that separation between the aqueous phase and the oil phase is less likely to occur, over long periods of time, than in the case in the oil-in-water emulsified compositions of comparative products.

<Preparation of Oil-in-Water Emulsified Compositions Containing a Powder>

Next, oil-in-water emulsified compositions were prepared that contained a powder resulting from thorough mixing, in equal amounts, silicone-treated talc, silicone-treated mica, silicone-treated sericite and silicone-treated titanium oxide (all products of SA-series, by Miyoshi Kasei, Inc.), and the stability of the prepared compositions was evaluated.

(Preparation Method)

Herein, starting material (III) and starting material (I-1) were charged into a 1000 mL beaker, which was then heated at 50° C. until starting material (I-1) had dissolved completely. Thereafter, starting material (II-1) was added while under stirring at the same temperature. Once addition was over, the whole was stirred continuously for 10 minutes, and, thereafter, the powder was added, with continuous stirring for a further 10 minutes, to cause the powder to disperse homogeneously, and yield as a result an oil-in-water emulsified composition (Inventive product 21). The blending proportions (mass %) of the various starting materials were as given in Table 9 below, so as to yield a total 500 g of the oil-in-water emulsified composition.

Oil-in-water emulsified compositions containing a powder (Inventive products 22 to 31) were obtained by being prepared in accordance with the same preparation method as that of the oil-in-water emulsified composition of Inventive product 21, but herein the starting materials and/or blending proportions thereof were modified as given in Table 9.

TABLE 9

| | Inventive products | | | | | | | | | | |
|---|---|---|---|---|---|---|---|---|---|---|---|
| | 21 | 22 | 23 | 24 | 25 | 26 | 27 | 28 | 29 | 30 | 31 |
| I-1 | 1 | — | — | — | — | — | 1 | 0.5 | 1 | 1 | 1 |
| I-2 | — | 1 | — | — | — | — | — | — | — | — | — |
| I-3 | — | — | 1 | — | — | — | — | — | — | — | — |
| I-4 | — | — | — | 1 | — | — | — | — | — | — | — |

TABLE 9-continued

| | Inventive products | | | | | | | | | | |
|---|---|---|---|---|---|---|---|---|---|---|---|
| | 21 | 22 | 23 | 24 | 25 | 26 | 27 | 28 | 29 | 30 | 31 |
| I-5 | — | — | — | — | 1 | — | — | — | — | — | — |
| I-6 | — | — | — | — | — | 1 | — | — | — | — | — |
| II-1 | 15 | 15 | 15 | 15 | 15 | 15 | — | — | 15 | 15 | 15 |
| II-2 | — | — | — | — | — | — | 15 | 35 | — | — | — |
| III | 69 | 69 | 69 | 69 | 69 | 69 | 69 | 29.5 | 64 | 64 | 64 |
| IV-1 | — | — | — | — | — | — | — | — | 5 | — | — |
| IV-2 | — | — | — | — | — | — | — | — | — | 5 | — |
| IV-3 | — | — | — | — | — | — | — | — | — | — | 5 |
| Powder | 15 | 15 | 15 | 15 | 15 | 15 | 15 | 35 | 15 | 15 | 15 |

Oil-in-water emulsified compositions containing a powder (Comparative products 20 to 30) were obtained by being prepared in accordance with the same preparation method as that of the oil-in-water emulsified composition of Inventive product 21, but herein the starting materials and/or blending proportions thereof were modified as given in Table 10.

TABLE 10

| | Comparative products | | | | | | | | | | |
|---|---|---|---|---|---|---|---|---|---|---|---|
| | 20 | 21 | 22 | 23 | 24 | 25 | 26 | 27 | 28 | 29 | 30 |
| I'-1 | 1 | — | — | — | — | — | — | — | — | — | — |
| I'-2 | — | 1 | — | — | — | — | — | — | 1 | — | — |
| I'-3 | — | — | 1 | — | — | — | — | — | — | — | — |
| I'-4 | — | — | — | 1 | — | — | — | — | — | — | — |
| I'-5 | — | — | — | — | 1 | — | — | — | — | — | — |
| I'-6 | — | — | — | — | — | 1 | — | — | — | 1 | — |
| I'-7 | — | — | — | — | — | — | 1 | — | — | — | — |
| I'-8 | — | — | — | — | — | — | — | 1 | — | — | 1 |
| II-1 | 15 | 15 | 15 | 15 | 15 | 15 | 15 | 15 | 15 | 15 | 15 |
| III | 69 | 69 | 69 | 69 | 69 | 69 | 69 | 69 | 64 | 64 | 64 |
| IV-2 | — | — | — | — | — | — | — | — | 5 | 5 | 5 |
| Powder | 15 | 15 | 15 | 15 | 15 | 15 | 15 | 35 | 15 | 15 | 15 |

Example 4: Evaluation of the Stability of Oil-in-Water Emulsified Compositions Containing a Powder The prepared oil-in-water emulsified compositions containing a powder of the above inventive products and comparative products were sealed in 100 mL screw tubes, and were left to stand in a thermostatic bath at 25° C. The state of each oil-in-water emulsified composition after one hour, one week, one month, two months, three months and four months after having been set in the thermostatic bath was observed visually, and was evaluated in accordance with the below-described criteria.

○: powder homogeneously dispersed
Δ: transparent oil phase slightly appreciable at the top of the oil-in-water emulsified composition
x: powder precipitated, and clearly observable separated oil phase at the top of the oil-in-water emulsified composition The evaluation results are given in Table 11. Instances of powder precipitation (rating x) were not further evaluated thereafter.

TABLE 11

| | Evaluation results for stability | | | | | |
|---|---|---|---|---|---|---|
| | 1 hour | 1 week | 1 month | 2 months | 3 months | 4 months |
| Inventive product 21 | ○ | ○ | ○ | Δ | X | — |
| Inventive product 22 | ○ | ○ | ○ | Δ | X | — |
| Inventive product 23 | ○ | ○ | ○ | Δ | X | — |
| Inventive product 24 | ○ | ○ | ○ | Δ | X | — |
| Inventive product 25 | ○ | ○ | ○ | Δ | X | — |
| Inventive product 26 | ○ | ○ | ○ | Δ | X | — |
| Inventive product 27 | ○ | ○ | ○ | Δ | X | — |
| Inventive product 28 | ○ | ○ | ○ | ○ | Δ | X |
| Inventive product 29 | ○ | ○ | ○ | ○ | ○ | Δ |
| Inventive product 30 | ○ | ○ | ○ | ○ | ○ | ○ |
| Inventive product 31 | ○ | ○ | ○ | ○ | ○ | Δ |
| Comparative product 20 | ○ | X | — | — | — | — |
| Comparative product 21 | ○ | X | — | — | — | — |
| Comparative product 22 | ○ | X | — | — | — | — |
| Comparative product 23 | ○ | X | — | — | — | — |
| Comparative product 24 | ○ | X | — | — | — | — |
| Comparative product 25 | X | — | — | — | — | — |
| Comparative product 26 | X | — | — | — | — | — |
| Comparative product 27 | X | — | — | — | — | — |
| Comparative product 28 | ○ | X | — | — | — | — |
| Comparative product 29 | X | — | — | — | — | — |
| Comparative product 30 | X | — | — | — | — | — |

As the results of Table 11 reveal, the oil-in-water emulsified compositions of inventive products exhibited superior stability, in that powder precipitation and/or separation between the aqueous phase and the oil phase is less likely to occur, over long periods of time, than in the case in the oil-in-water emulsified compositions of the comparative products.

The above results indicate that the present invention succeeds in providing an oil-in-water emulsified composition having excellent product stability and in which a powder that is added to the composition can be dispersed stably over long periods of time, without using any surfactant as an emulsifier, and in providing a cosmetic that contains the oil-in-water emulsified composition.

The present international application claims priority based on Japanese Patent Application No. 2012-261244, filed with the JPO on Nov. 29, 2012, and Japanese Patent Application No. 2013-090006, filed with the JPO on Apr. 23, 2013, the entire contents thereof being incorporated herein by reference.

The invention claimed is:

1. A urethane polymer obtained by a reaction of:
a monohydroxy compound (A) represented by Formula (1), $$R^1O\text{-}[C_2H_4\text{-}O]_m\text{-}H \quad (1)$$

wherein $R^1$ is an aliphatic hydrocarbon group having 24 to 36 carbon atoms, and m represents a number ranging from 0 to 1000;
a polyethylene glycol (B) represented by Formula (2), $$HO\text{-}[C_2H_4\text{-}O]_n\text{-}H \quad (2)$$

wherein n represents a number ranging from 20 to 500;
a monoglyceryl ether compound (C) represented by Formula (3), $$R^2\text{-}O\text{-}CH_2\text{-}CH\text{-}CH_2 \quad (3)$$
$$\phantom{R^2\text{-}O\text{-}CH_2\text{-}}|\phantom{\text{-}CH}|$$
$$\phantom{R^2\text{-}O\text{-}CH_2\text{-}}OH\phantom{}OH$$

wherein $R^2$ represents an aliphatic hydrocarbon group having 5 to 12 carbon atoms; and
an isocyanate compound (D) represented by Formula (4), $$R^3\text{-}[NCO]_q \quad (4)$$

wherein $R^3$ represents a hydrocarbon group having 6 to 13 carbon atoms, and q represents the number 2.

2. The urethane polymer according to claim 1, wherein a reaction ratio of the components is 10 to 30 moles of the monohydroxy compound (A), 5 to 20 moles of the monoglyceryl ether compound (C) and 20 to 50 moles of the isocyanate compound (D) with respect to 10 moles of the polyethylene glycol (B).

3. The urethane polymer according to claim 1, wherein the reaction is conducted through addition of the isocyanate compound (D) to a mixture of the monohydroxy compound (A), the polyethylene glycol (B) and the monoglyceryl ether compound (C).

* * * * *